US012773421B2

(12) United States Patent
De Marchi et al.

(10) Patent No.: US 12,773,421 B2
(45) Date of Patent: Oct. 27, 2026

(54) COMPOSITIONS AND METHODS USING A COMBINATION OF OLEUROPEIN AND QUERCETIN FOR USE IN CARTILAGE DEGENERATION

(71) Applicant: SOCIETE DES PRODUITS NESTLE S.A., Vevey (CH)

(72) Inventors: Umberto De Marchi, Corminboeuf (CH); Jerome Feige, Crissier (CH); Marie Noelle Horcajada, Echenevex (FR)

(73) Assignee: Societe des Produits Nestle S.A., Vevey (CH)

( * ) Notice: Subject to any disclaimer, the term of this patent is extended or adjusted under 35 U.S.C. 154(b) by 432 days.

(21) Appl. No.: 18/253,426

(22) PCT Filed: Nov. 16, 2021

(86) PCT No.: PCT/EP2021/081832
§ 371 (c)(1),
(2) Date: May 18, 2023

(87) PCT Pub. No.: WO2022/106410
PCT Pub. Date: May 27, 2022

(65) Prior Publication Data

US 2024/0009218 A1 Jan. 11, 2024

(30) Foreign Application Priority Data

Nov. 18, 2020 (EP) .................................... 20208394

(51) Int. Cl.

*A61K 31/7048* (2006.01)
*A61K 31/352* (2006.01)
*A61K 45/06* (2006.01)
*A61P 19/02* (2006.01)

(52) U.S. Cl.

CPC ........ *A61K 31/7048* (2013.01); *A61K 31/352* (2013.01); *A61K 45/06* (2013.01); *A61P 19/02* (2018.01)

(58) Field of Classification Search

CPC ............................ A61K 31/7048; A61P 19/02
See application file for complete search history.

(56) References Cited

U.S. PATENT DOCUMENTS

| | | | | |
|---|---|---|---|---|
| 2016/0120891 | A1* | 5/2016 | Horcajada .......... | A61K 36/9066 424/769 |
| 2019/0307828 | A1 | 10/2019 | Upadhyay et al. | |
| 2020/0108088 | A1 | 4/2020 | Horcajada et al. | |

FOREIGN PATENT DOCUMENTS

| | | | | |
|---|---|---|---|---|
| CN | 108686000 A | 10/2018 | | |
| JP | 2016524614 A | 8/2016 | | |
| WO | WO-0191734 A2 * | 12/2001 | ............. | A61P 19/10 |
| WO | 2014191447 | 12/2014 | | |
| WO | 2019092069 | 5/2019 | | |

OTHER PUBLICATIONS

Rosillo et al., Published Feb. 10, 2015, European Journal of Nutrition, vol. 55, pp. 315-325 (Year: 2015).*
Romani et al., Published Aug. 1, 2019, nutrients, vol. 11, Issue 8, pp. 1-33 (Year: 2019).*
Dell'Agli et al., Published Apr. 4, 2006, Journal of Agricultural and Food Chemistry, vol. 54, Issue 9, pp. 3259-3264 (Year: 2006).*
Polia et al., Published Nov. 1, 2022, Journal of Chromatography B, vol. 1210, pp. 1-10 (Year: 2022).*
Casas et al., Published Jan. 1, 2018, Endocrine, Metabolic, & Immune Disorders-Drug Targets, vol. 18, Issue 1, pp. 1-13 (Year: 2018).*
Ano "Application for the Approval of Bonolive (standardised olive leaf extract) Under Regulation (EC) No. 258/97 of the European Parliament and of the Council of Jan. 27, 1997 Concerning Novel Foods and Novel Food Ingredients Non-Confidential Dossier" Dec. 15, 2016, retrieved from the Internet at https://acnfp.food.gov.uk/sites/default/files/bonolive.nonconf.pdf, 77 pages, XP055822645.
Horcajada et al. "Oleuropein or rutin consumption decreases the spontaneous development of osteoarthritis in the Hartley guinea pig" Osteoarthritis and Cartilage, 2015, vol. 23, pp. 94-102.
Horcajada et al. "An Oleuropein-Based Dietary Supplement Improves Joint Functionality in Older People With High Knee Joint Pain" Abstracts, Osteoarthritis and Cartilage, 2020, vol. 28, 1 page (p. S472).
Guardia et al. "Anti-inflammatory properties of plant flavonoids. Effects of rutin, quercetin and hesperidin on adjuvant arthritis in rat" Il Farmaco, 2001, vol. 56, pp. 683-687.
Hu et al. "Quercetin alleviates rat osteoarthritis by inhibiting inflammation and apoptosis of chondrocytes, modulating synovial macrophages polarization to M2 macrophages" Free Radical Biology and Medicine, 2019, vol. 145, pp. 146-160.
Japanese Office Action for Appl No. 2023-528139 dated May 19, 2026, 4 pages.

* cited by examiner

*Primary Examiner* — Renee Claytor
*Assistant Examiner* — Jaret J Crews
(74) *Attorney, Agent, or Firm* — K&L Gates LLP

(57) ABSTRACT

The present invention relates to use of a composition comprising an effective amount of a combination of oleuropein and/or metabolite thereof and quercetin and/or derivative for maintenance of joint health or prevention or treatment of joint disorders in an individual. In particular, the invention relates to a composition comprising an effective amount of a combination of oleuropein and/or metabolite thereof and quercetin and/or derivative for use to prevent or treat cartilage degeneration in an individual.

13 Claims, 11 Drawing Sheets

COMPOSITIONS AND METHODS USING A COMBINATION OF OLEUROPEIN AND QUERCETIN FOR USE IN CARTILAGE DEGENERATION

CROSS REFERENCE TO RELATED APPLICATIONS

The present application is a National Stage of International Application No. PCT/EP2021/081832, filed on Nov. 16, 2021, which claims priority to European Patent Application No. 20208394.5, filed on Nov. 18, 2020, the entire contents of which are being incorporated herein by reference.

TECHNICAL FIELD OF THE INVENTION

The present invention relates to joint health and in particular to use of a composition comprising a combination of oleuropein and/or metabolite thereof and quercetin and/or metabolite thereof for prevention or treatment of joint disorders or maintenance of joint health.

BACKGROUND OF THE INVENTION

Osteoarthritis (OA) is a high prevalence disease with an important socio-economical impact. It is a degenerative disease of the articular cartilage of the joint, and is the most common form of arthritis, affecting 10% of the adult population. OA is the leading cause of disability in elderly and health care expenses throughout the world. The progressive degeneration and loss of the articular cartilage belongs to the main features of the pathology, accompanied by changes to other joint structures such as synovial membrane proliferation, sclerosis and thickness of subchondral bone, osteophyte formation at joint margin, ligament laxity and muscle atrophy, all of which contribute to the clinical symptoms of OA. These symptoms include severe pain, stiffness, loss of joint motion and disability. Because articular cartilage depends solely on its resident cells, the chondrocytes, for the maintenance of extracellular matrix, the compromising of chondrocyte function and survival would lead to the failure of the articular cartilage.

Recent ex vivo studies have reported mitochondrial dysfunction in human OA chondrocytes, and analyses of mitochondrial electron transport chain activity in these cells showed decreased activity of Complexes I, II and III compared to normal chondrocytes and low ATP production. This mitochondrial dysfunction may affect several pathways that have been implicated in cartilage degeneration, including oxidative stress, defective chondrocyte biosynthesis and growth responses, increased cytokine induced chondrocyte inflammation and matrix catabolism, cartilage matrix calcification, and increased chondrocyte apoptosis (Blanco et al. "The role of mitochondria in osteoarthritis" Nat. Rev. Rheumatol. 7, 161-169 (2011).

Mitochondria are the primary source of aerobic energy production in mammalian cells and also maintain a large Ca2+ gradient across their inner membrane, providing a signaling potential for this molecule. Furthermore, mitochondrial Ca2+ plays a role in the mitochondria in the regulation of ATP generation and potentially contributes to the orchestration of cellular metabolic homeostasis. (Glancy, B. and R. S. Balaban (2012). "Role of mitochondrial Ca2+ in the regulation of cellular energetics." Biochemistry 51(14): 2959-2973).

Although there is an increase of individuals suffering from OA, there is still no cure and current medical therapies remain only palliative, focused on alleviation of symptoms. For example, pain and inflammation are treated using analgesics (such as acetaminophen) and non-steroidal anti-inflammatory drugs (NSAIDs). Furthermore, the use of these drugs is often associated with side effects such as gastrointestinal or cardiovascular risks. Because current treatments for OA do not prevent or cure OA, chondrocyte apoptosis would be a valid target to modulate cartilage degeneration.

SUMMARY OF THE INVENTION

The inventors have surprisingly demonstrated that a combination of oleuropein (or oleuropein aglycone) and quercetin synergistically activates mitochondrial function at the cellular level, via mitochondrial calcium elevation.

An object of the present invention therefore relates to providing compositions for use in improving joint health. In particular, it is an object of the present invention to provide compositions which improve joint health by preventing or treating cartilage degeneration, and solves the above mentioned problems of the prior art with regards to side effects such as gastrointestinal and/or cardiovascular risks.

Thus, one aspect of the invention relates to a composition comprising an effective amount of a combination of oleuropein and/or metabolite thereof and quercetin and/or derivative thereof for use to prevent or treat cartilage degeneration in an individual.

Another aspect of the present invention relates to a method of manufacturing a composition for use according to the invention.

In a last aspect, the present invention relates to a kit comprising an effective amount of a combination of oleuropein and/or a metabolite thereof and quercetin and/or a derivative thereof in one or more containers.

Additional features and advantages are described herein and will be apparent from the following Figures and Detailed Description.

BRIEF DESCRIPTION OF THE FIGURES

FIG. 5A is a graph showing that collagen-IIα1 content is strongly decreased in that model compared with control chondrocytes. In addition, FIGS. 5B and 5C are two graphs showing that the expression of metalloproteinases MMP3 (FIG. 5B) and MMP13 (FIG. 5C) are increased in IL-1β-treated cells. Results are expressed as mean+/−SEM from n=5 (FIG. 5A) or n=3 (FIG. 5B) or n=4 (FIG. 5C) experiments per condition. * indicates statistically significant difference of control vs. SW1353 cells treated with IL-1β for 24 h or 48 h, as indicated, at P<0.05 (One-way ANOVA test).

FIG. 9A is a western blot showing that the expression of MCU is reduced in MCU-ablated SW1353 cells (MCU-kd). As shown in FIGS. 9B and 9C, collagen-IIα1 content and aggrecan content, respectively, are strongly decreased when the expression of MCU, the transporter which mediates the uptake of calcium in mitochondria, is decreased. In addition, FIG. 9D is a graph showing that the expression of metalloproteinases MMP3 is increased in MCU-depleted cells. Results are expressed as mean+/−SEM from n=3 experiments per condition in each graph (FIGS. 9B,C,D). * indicates statistically significant difference of control vs. MCU-depleted cells, as indicated, at P<0.05 (One-way ANOVA test).

DETAILED DESCRIPTION OF THE INVENTION

Definitions

Figure 1:
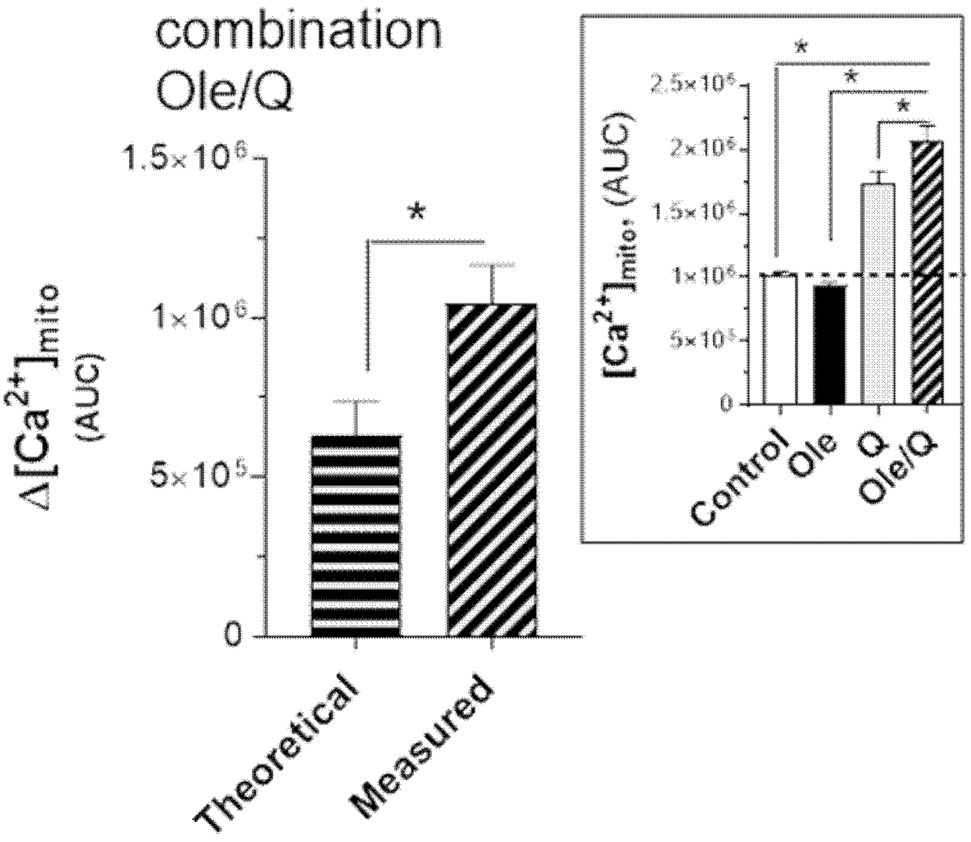
FIG. 1 is a graph showing that oleuropein (Ole) synergies with Quercetin (Q) to activate mitochondria via mitochondrial Ca2+ rise, during HeLa cells stimulation. The inset shows the effect of oleuropein (3 μM, black), quercetin (3 μM, gray) and the combination of 3 μM oleuropein+3 μM quercetin (Ole/Q) on the integrated mitochondrial calcium rise, evoked by 100 μM histamine. The data in the inset were used to determine, in the main figure, the expected theoretical effect (sum between oleuropein effect and quercetin effect) and the real measured effect of the combination (oleuropein+quercetin, Ole/Q) and to extrapolate the synergism. Results are expressed as mean+/−SEM from n=6-9 experiments. * indicates statistically significant difference of the measured vs. theoretical difference in mitochondrial calcium at $P<0.05$ (Student's t-test).

Prior to discussing the present invention in further details, the following terms and conventions will first be defined:

In the context of the present invention, mentioned percentages are weight/weight percentages unless otherwise stated.

The term "and/or" used in the context of the "X and/or Y" should be interpreted as "X", or "Y", or "X and Y".

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 8, from 3 to 7, from 4 to 9, from 3.6 to 4.6, from 3.5 to 9.9, and so forth.

The terms "prevent" and "prevention" mean to administer a composition as disclosed herein to a subject is not showing any symptoms of the condition to reduce or prevent development of at least one symptom associated with the condition. Furthermore, "prevention" includes reduction of risk, incidence and/or severity of a condition or disorder.

As used herein, an "effective amount" is an amount that treats or prevents a deficiency, treats or prevents a disease or medical condition in an individual, or, more generally, reduces symptoms, manages progression of the disease, or provides a nutritional, physiological, or medical benefit to the individual.

"Animal" includes, but is not limited to, mammals, which includes but is not limited to rodents; aquatic mammals; domestic animals such as dogs, cats and other pets; farm animals such as sheep, pigs, cows and horses; and humans. Where "animal," "mammal" or a plural thereof is used, these terms also apply to any animal that is capable of the effect exhibited or intended to be exhibited by the context of the passage, e.g., an animal benefitting from improved mitochondrial calcium import. While the term "individual" or "subject" is often used herein to refer to a human, the present disclosure is not so limited. Accordingly, the term "individual" or "subject" refers to any animal, mammal or human that can benefit from the methods and compositions disclosed herein.

The term "pet" means any animal which could benefit from or enjoy the compositions provided by the present disclosure. For example, the pet can be an avian, bovine, canine, equine, feline, hircine, lupine, murine, ovine, or porcine animal, but the pet can be any suitable animal. The term "companion animal" means a dog or a cat.

A "subject" or "individual" is a mammal, preferably a human. The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals. The term "older adult" in the context of a human means an age from birth of at least 45 years, preferably above 50 years, more preferably above 55 years, and includes elderly individuals.

An "oral nutrition supplement" or "ONS" is a composition comprising at least one macronutrient and/or at least one micronutrient, for example in a form of sterile liquids, semi-solids or powders, and intended to supplement other nutritional intake such as that from food. Non-limiting examples of commercially available ONS products include MERITENE®, BOOST®, NUTREN® and SUSTAGEN®. In some embodiments, an ONS can be a beverage in liquid form that can be consumed without further addition of liquid, for example an amount of the liquid that is one serving of the composition.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

All references to singular characteristics or limitations of the present invention shall include the corresponding plural characteristic or limitation, and vice versa, unless otherwise specified or clearly implied to the contrary by the context in which the reference is made.

Unless defined otherwise, all technical and scientific terms used herein have the same meaning as commonly understood by one of ordinary skill in the art.

Composition for Use

Joint disease may be accompanied by inflammation to a greater or lesser degree. In some diseases, the inflammation is an overriding component, such as for example in Rheumatoid arthritis (RA). In other diseases, such as for example OA, the inflammation does not appear as prominently. However, both diseases have a catabolic component in which the articular cartilage is broken down.

The present inventors have shown that the provision of a combination of oleuropein and/or metabolite thereof and quercetin and/or derivative synergistically improves mitochondrial functions which are altered in osteoarthritis for example.

Thus, the invention in a first aspect relates to a composition comprising an effective amount of a combination of oleuropein and/or metabolite thereof and quercetin and/or derivative thereof for use to improve joint health, for example to prevent or treat cartilage degeneration in an individual.

In another manner, this aspect of the invention may be described as the use of an effective amount of a combination of oleuropein and/or metabolite thereof and quercetin and/or derivative thereof in the manufacture of a medicament for the prevention or treatment of cartilage degeneration in an individual.

The use to prevent or treat cartilage degeneration is synonymous with use to inhibit or decrease cartilage degeneration.

Embodiments of the invention thus include a composition comprising an effective amount of a combination of oleuropein and/or metabolite thereof and quercetin and/or derivative thereof for use to prevent or treat cartilage degeneration.

Further embodiments of the invention include a composition for use according to the invention, wherein the composition further comprises calcium.

Ingredients—Main Bioactive Compounds

The oleuropein and quercetin are the main bioactive molecules according to present invention.

Oleuropein is a polyphenol found in the fruit, the roots, the trunk and more particularly in the leaves of plants belonging to the Oleaceae family, and especially *Olea europaea*.

In an embodiment, at least a portion of the oleuropein is obtained by extraction, e.g., by extraction from a plant such as a plant belonging to the Oleaceae family, preferably one or more of the stems, the leaves, the fruits or the stones of a plant belonging to the Oleaceae family such as *Olea europaea* (olive tree), a plant of genus *Ligustrum*, a plant of genus *Syringa*, a plant of genus *Fraximus*, a plant of genus *Jasminum* and a plant of genus Osmanthus. Additionally or alternatively, at least a portion of the oleuropein and/or metabolites can be obtained by chemical synthesis.

Non-limiting examples of suitable metabolites of oleuropein include oleuropein aglycone, hydroxytyrosol, elenolic acid, homovanillyl alcohol, isohomovanillyl alcohol, glucuronidated forms thereof, sulfated forms thereof, derivatives thereof, and mixtures thereof.

Quercetin is the aglycone form of a number of other flavonoid glycosides, such as rutin and quercitrin, found in citrus fruit, buckwheat and onions. Quercetin comes from the glycosides quercitrin and rutin together with rhamnose and rutinose, respectively.

Likewise guaijaverin is the 3-O-arabinoside, hyperoside is the 3-O-galactoside, isoquercitin is the 3-O-glucoside and spiraeoside is the 4'-O-glucoside. Miquelianin is the quercetin 3-O-β-D-glucuronopyranoside.

In a preferred embodiment, the derivative of quercetin may be selected from the group consisting of quercetin 3-O-galactoside, quercetin 3-O-glucoside (izoquercetin), quercetin 3-O-xyloside, quercetin 3-O-rhamnoside (quercitrin), quercetin 3-O-glucuronide, quercetin 7-O-glucoside, quercetin 3-O-diglucoside, quercetin 3,4'-diglucoside, quercetin 3-O-rhamnoside-70-glucoside, quercetin 3-O-rutinoside (rutin), quercetin 3-O-6"-acetylglucoside, quercetin 3-methyl ether, quercetin 3,3'-dimethyl ether, and mixtures thereof.

The quercetin may be from any suitable source and may be isolated and/or chemically synthesized.

In a preferred embodiment oleuropein and quercetin and derivatives are obtained from plant sources. For example, oleuropein may be obtained from olive plants, rutin may be obtained from onions, quercetin may be obtained from onions, green tea, apples, berries, *Ginkgo biloba*, St. John's wort, American elder, buckwheat tea and others.

The effective amount of each of the oleuropein and/or metabolite thereof and quercetin and/or derivative thereof varies with the particular composition, the age and condition of the recipient, and the particular disorder or disease being treated. Nevertheless, in a general embodiment, 0.001 mg to 1.0 g can be administered to the individual per day, preferably from 0.01 mg to 0.9 g per day, more preferably from 0.1 mg to 750 mg per day, more preferably from mg to 500 mg per day, and most preferably from 1.0 mg to 200 mg per day. Moreover, the inventors found that the active dose of oleuropein or derivative in the combination, may be lowered for an equal efficacy.

In some embodiments, the combination of oleuropein or metabolite and the quercetin or derivative is administered in a composition further comprising calcium. At least a portion of the calcium can be one or more calcium salts, such as calcium acetate, calcium carbonate, calcium chloride, calcium citrate, calcium glubionate, calcium gluconate, calcium lactate or mixtures thereof. In a general embodiment, 0.1 g to 1.0 g of the calcium is administered to the individual per day, preferably from 125 mg to 950 g of the calcium per day, more preferably from 150 mg to 900 mg of the calcium per day, more preferably from 175 mg to 850 mg of the calcium per day, and most preferably from 200 mg-800 mg of the calcium per day.

In an alternative embodiment, the combination of oleuropein and quercetin can be administered sequentially with calcium in separate compositions. The term "sequentially" means that the calcium and the at least one of oleuropein or metabolite thereof are administered in a successive manner such that the at least one of oleuropein or metabolite thereof is administered at a first time without the calcium, and the calcium is administered at a second time (before or subsequent to the first time) without the combination of oleuropein and quercetin. The time between sequential administrations may be, for example, one or several seconds, minutes or hours in the same day; one or several days or weeks in the same month; or one or several months in the same year.

In some embodiments, the oleuropein or metabolite thereof and the quercetin or derivative thereof are the only polyphenols in the composition and/or the only polyphenols administered to the individual.

The composition can comprise an effective amount of at least one of oleuropein or metabolite thereof. For example, a single serving or dose of the composition can comprise the effective amount, and a package can contain one or more of the servings or doses. Optionally the composition can further comprise calcium.

In another embodiment, the oleuropein and/or derivative can be provided by any of the compositions and methods disclosed by WO 2019/092068 and WO 2019/092066, each entitled "Bioconversion of oleuropein" and "Method of selecting a probiotic", and WO 2019/092069 entitled "Homovanillyl alcohol (HVA), HVA isomer, methods of making compositions comprising such compounds, and methods of using such compounds", each incorporated herein by reference in its entirety.

Ingredients—Further Bioactive Compound

The compositions for use according to the invention may also comprise at least one further bioactive compound selected from the group consisting of antioxidants, anti-inflammatory compounds, glycosaminoglycans, prebiotics, fibres, probiotics, fatty acids, enzymes, minerals, trace elements and/or vitamins.

The term "bioactive" in the context of the present application means that the compound contributes to the health of an individual, or has an effect on the human body, beyond that of meeting basic nutritional need.

The at least one further bioactive compound may be from a natural source. Thus the compounds may be from extracts of plants, animals, fish, fungi, algae, microbial fermentation. Minerals are considered as from natural source also within this definition.

In a preferred embodiment, enzymes may be proteases such as trypsin, or enzyme extracts such as bromelain, for example.

Nutritional Compositions

The compositions for use according to the invention may be nutritional compositions or pharmaceutical compositions, and may be for human or veterinary use.

Thus, in preferred embodiments, the composition for use according to the invention is a nutritional composition.

By "nutritional composition" is meant in the context of the present application a composition which is a source of nutrition to an individual.

The nutritional products or compositions of the invention may be a source of complete nutrition or may be a source of incomplete nutrition.

As used herein, "complete nutrition" includes nutritional products and compositions that contain sufficient types and levels of macronutrients (protein, fats and carbohydrates) and micronutrients to be sufficient to be a sole source of nutrition for the animal to which it is being administered to. Patients can receive 100% of their nutritional requirements from such complete nutritional compositions.

As used herein, "incomplete nutrition" includes nutritional products or compositions that do not contain sufficient levels of macronutrients (protein, fats and carbohydrates) or micronutrients to be sufficient to be a sole source of nutrition for the animal to which it is being administered to. Partial or incomplete nutritional compositions can be used as a nutritional supplement.

The combination of oleuropein and quercetin can be administered in any composition that is suitable for human and/or animal consumption. In a preferred embodiment, it is administered to the individual orally or enterally (e.g. tube feeding). For example, it can be administered to the individual in a beverage, a food product, a capsule, a tablet, a powder or a suspension.

Non-limiting examples of suitable compositions for the include food compositions, dietary supplements, dietary supplements (e.g., liquid ONS), complete nutritional compositions, beverages, pharmaceuticals, oral nutritional supplement, medical food, nutraceuticals, food for special medical purpose (FSMP), powdered nutritional products to be reconstituted in water or milk before consumption, food additives, medicaments, drinks, petfood, and combinations thereof.

Nutritional Composition Ingredients

Protein Source

In an embodiment, the compositions for use according to the invention include a source of protein. The protein source may be dietary protein including, but not limited to animal protein (such as milk protein, meat protein or egg protein), vegetable protein (such as soy protein, wheat protein, rice protein, and pea protein), or combinations thereof. In an embodiment, the protein is selected from the group consisting of whey, chicken, corn, caseinate, wheat, flax, soy, carob, pea or combinations thereof.

Carbohydrate Source

In an embodiment, the compositions include a source of carbohydrates. Any suitable carbohydrate may be used in the present compositions including, but not limited to, starch, sucrose, lactose, glucose, fructose, corn syrup solids, maltodextrin, modified starch, amylose starch, tapioca starch, corn starch, xylitol, sorbitol or combinations thereof.

Fat Source

In an embodiment, the compositions include a source of fat. The source of fat may include any suitable fat or fat mixture. For example, the fat source may include, but is not limited to, vegetable fat (such as olive oil, corn oil, sunflower oil, high-oleic sunflower, rapeseed oil, canola oil, hazelnut oil, soy oil, palm oil, coconut oil, blackcurrant seed oil, borage oil, lecithins, and the like), animal fats (such as milk fat), or combinations thereof. The source of fat may also be less refined versions of the fats listed above (e.g., olive oil for polyphenol content).

Flavourings Etc.

In addition, compositions for use according to the invention may also comprise natural or artificial flavours, for example fruit flavours like banana, orange, peach, pineapple or raspberry or other plant flavours like vanilla, cocoa, coffee, etc.

Nutritional Composition Formats

The nutritional compositions may include, besides the main bioactive components and any further bioactive components, and optionally one or more of a protein, carbohydrate and fat source, any number of optional additional food ingredients, including conventional food additives (synthetic or natural), for example one or more acidulants, additional thickeners, buffers or agents for pH adjustment, chelating agents, colorants, emulsifiers, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

The nutritional composition may be provided in any suitable format.

Examples of nutritional composition formats in which the composition for use according to the invention may be provided include solutions, ready-for-consumption compositions (e.g. ready-to-drink compositions or instant drinks), liquid comestibles, soft drinks, juice, sports drinks, milk drinks, milk-shakes, yogurt drinks, soup, etc.

In a other embodiments, the nutritional compositions may be provided in the form of a concentrate, a powder, or granules (e.g. effervescent granules), which are diluted with water or other liquid, such as milk or fruit juice, to yield the ready-for-consumption composition.

Further nutritional composition formats include, baked products, dairy products, desserts, confectionery products, cereal bars, and breakfast cereals. Examples of dairy products include milk and milk drinks, yoghurts and other cultured milk products, ice creams and cheeses. Examples of baked products include bread, biscuits and cakes.

In one embodiment, the composition for use according to the invention may also be available in a great variety of formats designed as animal foods, in particular for the dog or the cat, whether in a wet form, semi-wet form or dry form, in particular in the form of biscuits.

Routes of Administration

The nutritional compositions of the present disclosure may be administered by any means suitable for human administration, and in particular for administration in any part of the gastrointestinal tract. Enteral administration, oral administration, and administration through a tube or catheter are all covered by the present disclosure. The nutritional compositions may also be administered by means selected from oral, rectal, sublingual, sublabial, buccal, topical, etc.

The nutritional compositions may be administered in any known form including, for example, tablets, capsules, liquids, chewables, soft gels, sachets, powders, syrups, liquid suspensions, emulsions and solutions in convenient dosage forms. In soft capsules, the active ingredients are preferably dissolved or suspended in suitable liquids, such as fatty oils, paraffin oil or liquid polyethylene glycols. Optionally, stabilizers may be added.

If the nutritional compositions are administered by tube feeding, the nutritional compositions may be used for short term or long term tube feeding.

Inhibit or Decrease Cartilage Degeneration

Cartilage degeneration may be a result of pathology (either chronic or acute), trauma, or combinations thereof.

Cartilage degeneration takes place both in pathologies dominated by inflammation (such as rheumatoid arthritis) as well as in pathologies where inflammation is not as prominent (eg osteoarthritis).

Trauma can also result in cartilage degeneration processes being initiated. For example, tearing a ligament in the knee leads to destabilization of the knee joint, and degeneration processes will be initiated.

Trauma in the context of the present application refers to a physiological injury caused by an external source, such as for example by falling, or being impacted by a car etc. Trauma may also be the accumulation of small insults over time, so called "wear and tear".

While often it is preferred to treat trauma with surgery, in one embodiment the present invention relates to a method of treatment where trauma is treated by surgery and also by administering a composition of the invention.

Thus, embodiments of the use according to the invention include use to inhibit or decrease cartilage degeneration, wherein the cartilage degeneration is a result of a pathology or of trauma.

Examples of pathologies involving cartilage degeneration, and where the compositions of the invention may therefore be useful, include Osteoarthritis, Rheumatoid arthritis, Gout and pseudo-gout, Septic arthritis, Ankylosing spondylitis, Juvenile idiopathic arthritis, Still's disease, Psoriasis (Psoriatic arthritis), Reactive arthritis, Ehlers-Danlos Syndrome, Haemochromatosis, Hepatitis, Lyme disease, Inflammatory bowel disease (Including Crohn's Disease and Ulcerative Colitis), Henoch-Schönlein purpura, Hyperimmunoglobulinemia D with recurrent fever, Sarcoidosis, TNF receptor associated periodic syndrome, Wegener's granulomatosis (and many other vasculitis syndromes), Familial Mediterranean fever, Systemic lupus erythematosus.

In preferred embodiments, the composition of the invention is for use to inhibit or decrease cartilage degeneration in RA and/or OA.

In a further preferred embodiment, the composition of the invention is for use to inhibit or decrease cartilage degeneration in OA.

Additionally, without wishing to be bound by theory it has been observed that while inflammation often leads to cartilage degeneration in joints, cartilage degeneration does also occur in situations where the inflammatory component is much less pronounced, and perhaps even negligible.

For example, trauma to a joint may well initiate cartilage degeneration, without the prominent inflammatory component present for example in RA.

Trauma may for example involve tearing ligaments, or impact trauma to a joint for example the knee, fingers.

In another example, OA is primarily a joint degenerative disease, with a lesser inflammatory component.

Thus, the invention in one embodiment relates to a composition for use according to the invention to inhibit or decrease cartilage degeneration, and wherein the cartilage degeneration takes place in the context of a pathology with little or no inflammatory component, such as trauma or for example OA.

Use to Counteract Early Degeneration Events

Hypertrophy suggests catabolic activity of the chondrocyte which is not a normal phenotype.

Thus, the invention in one embodiment relates to a composition according to the invention comprising a combination of oleuropein and/or metabolite thereof and quercetin and/or derivative for use to inhibit or decrease hypertrophy of chondrocytes, which is one early event indicative of degeneration of cartilage.

Treat or Prevent Decreased Mobility with Age

The compositions for use according to the invention have been shown to inhibit or decrease proteolytic activity.

Ageing leads to cartilage degeneration.

Thus, the invention relates to a composition of the invention for use to inhibit or decrease cartilage degeneration associated with ageing.

In another embodiment, the invention relates to a composition of the invention for use to inhibit or decrease collagen degeneration in cartilage degeneration associated with ageing, for example use to inhibit or prevent collagen II degeneration in cartilage associated with ageing.

The degeneration of cartilage can contribute to joint stiffness and joint pain, leading to decreased mobility in the patient.

The compositions for use according to the invention may in other embodiments be used for i) maintaining or improving joint functionality, including cartilage functionality, during ageing, ii) decrease joint pain including inflammatory and/or nociceptive pain.

In a further embodiment the invention relates to a composition for use according to the invention to improve mobility in a subject, for example in adult or elderly mammals.

Thus, in a preferred embodiment the composition according the invention may be for use to improve activity and/or mobility of the individual, for example by preventing or treating osteoarthritis, and/or by inhibiting or decreasing cartilage degeneration.

Other preferred embodiments relate to a composition for use according to the invention wherein the use is to prevent cartilage degeneration and thus maintain healthy joints, or to maintain or improve mobility, prevent or decrease joint pain (inflammatory and/or nociceptive pain). In a further embodiment the compositions of the invention may be for use to maintain the status of the cartilage.

Target Groups

Target groups for the composition for use according to the invention may be any mammal displaying cartilage degeneration, for example because they suffer from one or more of the pathologies involving cartilage degeneration mentioned herein. Cartilage degeneration may be detected by visual means, such as by radiography. Alternatively, the detection of degeneration products of cartilage may detected in bodily fluid. For example one or more collagen II epitopes such as (Coll2-1, Coll2-1 NO2, CTX-II) may be detected in for example samples, such as plasma or urine samples.

Another target group may be any mammal who does not yet display cartilage degeneration, but who are at risk for cartilage degeneration, for example at risk for OA, RA or any of the pathologies involving cartilage degeneration mentioned herein. In a preferred embodiment, the invention relates to a composition according to the invention comprising a combination of oleuropein or metabolite thereof and quercetin or derivative for use to inhibit or decrease early degeneration of cartilage, is administered to this target group.

A particular embodiment of the invention relates to the composition for use to improve activity and/or mobility of the individual, for example by preventing, or treating osteoarthritis, and/or by inhibiting or decreasing cartilage degeneration in elderly or aging individuals.

In further embodiments, the composition for use according to the invention may be for use in mammals, such as humans, or pets. Examples of pets include cats, dogs, and horses.

Though the invention may be useful in many various age groups, in a preferred embodiment the compositions for use to increase mobility according to the invention are targeted to ageing population, in particular healthy aging and/or elderly mammals.

Method of Manufacturing a Nutritional Composition of the Invention

The invention relates in a further aspect to a method for manufacturing a nutritional composition for use according to the invention, said method comprising the step of:

providing ingredients for a nutritional composition comprising a combination of oleuropein and/or metabolite thereof and quercetin and/or derivative thereof, and mixing, such that the nutritional composition comprises the combination of oleuropein and/or metabolite thereof and quercetin and/or derivative thereof.

Pharmaceutical Composition for Use

In a further embodiment, the invention relates to a composition for use to inhibit or prevent cartilage degeneration according to the invention, wherein the composition is a pharmaceutical composition.

By pharmaceutical means a composition, other than a nutritional composition, wherein a substance is used on or in the body to prevent, diagnose, alleviate, treat, or cure a disease in humans or animals in medicine. According to the present invention, the pharmaceutical may be used for inhibiting or decreasing cartilage degeneration.

The pharmaceutical may be for use by a human. It may alternatively be a veterinary composition, for example suited for a dog, cat, or horse, in particular a thoroughbred horse.

In one preferred embodiment, the pharmaceutical composition of the invention comprises a combination of oleuropein or metabolite thereof and quercetin or derivative.

In another preferred embodiment, the pharmaceutical composition of the invention comprises oleuropein or metabolite thereof and quercetin or derivative and curcumin.

The invention further relates to uses of the pharmaceutical according to the invention, as described herein as use of the compositions of the invention.

A pharmaceutical composition for use according to the invention comprising a combination of oleuropein or metabolite thereof and quercetin or derivative and/or curcumin in combination with at least one excipient selected from the group constituted by the pharmaceutically acceptable excipients. Procedures for the preparation of pharmaceutical compositions according to the invention can easily be found by the specialist skilled in the art, for example in the handbook Remington's Pharmaceutical Sciences, Mid. Publishing Co, Easton, Pa., USA. Physiologically acceptable excipients, vehicles and adjuvants are also described in the handbook entitled "Handbook of Pharmaceutical Excipients, Second edition, American Pharmaceutical Association, 1994. In order to formulate a pharmaceutical composition according to the invention, the specialist skilled in the art will advantageously be able to refer to the latest edition of the European Pharmacopoeia or the Pharmacopoeia of the United States of America (USP). The specialist skilled in the art will in particular be able advantageously to refer to the fourth edition "2002" of the European Pharmacopoeia or also to the edition USP 25-NF 20 of the American Pharmacopoeia (U.S. Pharmacopoeia).

Advantageously, a pharmaceutical composition such as defined above is suitable for oral, parenteral or intravenous administration. When the pharmaceutical composition for use according to the invention comprises at least one pharmaceutically or physiologically acceptable excipient, it is in particular an excipient appropriate for administration of the composition by the oral route or an excipient suitable for administration of the composition by the parenteral route.

A pharmaceutical composition for use according to the invention is available indifferently in a solid or liquid form. For oral administration, a solid pharmaceutical composition in the form of tablets, capsules or gelatine capsules will be preferred.

In liquid form, a pharmaceutical composition in the form of an aqueous or non-aqueous suspension, or also in the form of a water-in-oil or oil-in-water emulsion will be preferred.

Solid pharmaceutical forms may comprise, as vehicles, adjuvants or excipients, at least one diluent, one flavour, one solubilising agent, one lubricant, one suspension agent, one binder, one disintegrating agent and one encapsulating agent. Such compounds are for example magnesium carbonate, magnesium stearate, talc, lactose, pectin, dextrin, starch, gelatine, cellulosic materials, cocoa butter, etc. The compositions in liquid form may also comprise water, possibly as a mixture with propylene glycol or polyethylene glycol, and possibly also colouring agents, flavours, stabilisers and thickening agents.

Combination with Known Treatments

In this context of lack of disease-modifying OA drugs (DMOAD), alternative treatments and OA prevention could come from nutrition.

It can be seen from the histological data that oleoeuropein has a greater effect on OA score than compounds which mainly effect the degeneration. The efficiency of oleoeuropein may thus be due to the combined effect on inflammation and degeneration. Therefore, in preferred embodiments, the composition of the invention, which has been shown to inhibit or decrease degeneration, may be combined with treatments for inhibiting or decreasing inflammation.

Method of Treatment

The invention also relates to a method of prevention or treatment of cartilage degeneration, for example a pathology in which cartilage degeneration takes place or a trauma which is associated with cartilage degeneration, said method comprising administering to an individual in need thereof an effective amount of a composition according to the invention. For example, the method comprises administering an effective amount of a composition comprising a combination of oleuropein or metabolite thereof and quercetin or derivative.

As used herein, "effective amount" is an amount that prevents a deficiency, treats a disease or medical condition in an individual or, more generally, reduces symptoms, manages progression of the diseases or provides a nutritional, physiological, or medical benefit to the individual.

The effective amount of a composition according to the present invention which is required to achieve a therapeutical effect will, of course, vary with the particular composition, the route of administration, the age and condition of the recipient, and the particular disorder or disease being treated.

The invention further provides methods of preventing or treating pathologies involving cartilage degeneration, such as for example OA or RA; inhibiting or decreasing cartilage degeneration; inhibiting or decreasing collagen degeneration in cartilage; inhibiting or decreasing collagen II degeneration in cartilage; which methods comprise administering an effective amount of a composition for use according to the invention to an individual.

In one embodiment, the method of treatment according to the invention concerns preventing or treating osteoarthritis.

The methods of treatment according to the invention may be in a mammal, such as a human, or a pet, for example a dog, a cat and/or a horse.

In certain embodiments the composition of the invention to be administered in the method of treatment, may be one or more nutritional compositions of the invention and/or pharmaceutical compositions of the invention.

Kit

The present disclosure also provides a kit comprising a combination of a combination of oleuropein and/or a metabolite thereof and quercetin and/or a derivative in one or more containers. In an embodiment of the kit, the one or more containers comprise at least one first container that stores the oleuropein and/or metabolite separately from the quercetin and/or derivative, which is stored in at least one second container, and the kit further comprises instructions for admixing the oleuropein with the quercetin into a unit dosage form.

In an embodiment of the kit, the combination can be provided together in one or more prepackaged unit dosage forms, for example in separate containers that each contain a dried powder such that each container contains one pre-packaged unit dosage form.

In another embodiment, the kit can comprise a plurality of compositions for admixing together to form one or more of the compositions disclosed herein. For example, the kit can contain two or more dried powders in separate containers relative to each other, the separate powders each containing a portion of the final unit dosage form. As a non-limiting example of such an embodiment, the kit can contain one or more first containers that house the oleuropein and can also contain one or more second containers that house the quercetin. The content of one of the first containers can be admixed with one of the second containers to form at least a portion of the unit dosage form of the composition.

The above examples of administration do not require continuous daily administration with no interruptions. Instead, there may be some short breaks in the administration, such as a break of two to four days during the period of administration. The ideal duration of the administration of the composition can be determined by those of skill in the art.

Combination of Disclosures

It should be noted that embodiments and features described in the context of one of the aspects of the present invention also apply to the other aspects of the invention.

The compositions for use according to the invention are herein described in different parameters, such as the ingredients, nutritional composition formats, uses, target groups etc. It should be noted that embodiments and features described in the context of one of the parameters of the composition for use according to the invention, may also be combined with other embodiments and features described in the context of another parameter, unless expressly stated otherwise.

All patent and non-patent references cited in the present application, are hereby incorporated by reference in their entirety.

The invention will now be described in further details in the following non-limiting examples.

EXAMPLES

The following non-limiting examples present experimental data supporting the compositions and methods disclosed herein.

Example 1

To test the effect of oleuropein (or oleuropein aglycone), quercetin and their combination in living cells, the inventors measured mitochondrial calcium elevation in HeLa cells. HeLa cells were purchased from ATCC. HeLa cells were seeded in 96-well plates at a density of 50000 cells per well in minimal essential medium (DMEM, Gibco), high glucose, +10% fetal calf serum. Mitochondrial calcium measurements were carried out using Hela cells infected with the adenovirus (from Sirion biotech) expressing the mitochondrially targeted calcium sensor mitochondrial mutated aequorin (Montero et al., 2004). For aequorin reconstitution, 24 hours after infection, cells were incubated for 2 h at room temperature (22±° C.) in standard medium (145 mM NaCl, 5 mM KCl, 1 mM $MgCl_2$, 1 mM $CaCl_2$), 10 mM glucose and 10 mM Hepes, pH 7.4) with 1 μM wild-type coelenterazine. For treatment, compounds were directly added to the cell culture or myotubes cultures 2 hours before measurements. Luminescence was measured at the FLIPR Tetra Aequorin (Molecular Devices). Mitochondrial calcium rise was obtained by stimulating the cells with 100 μM histamine. Calibration of the luminescence data into calcium concentration was carried out using an algorithm, as described previously (Alvarez & Montero, 2002). Custom module analysis based on Excel (Microsoft) and GraphPad Prism 7.02 (Graph Pad) software was used for quantification.

To validate the effect of the pro-inflammatory cytokine Interleukin-1β as an osteoarthritis-mimetic in a chondrocyte cellular model and to test the effect of the mitochondrial calcium uniporter (MCU) ablation on chondrocyte function, the inventors measured chondrocyte function and mitochondrial function in SW1353 cells. SW1353 cells were purchased from ATCC. SW1353 cells were seeded in 96-well plates at a density of 10 000 cells per well in 100 mm dishes (for mitochondrial calcium measurement) or at a density of 1 000 000 cells (for western blots). Cells were cultured in minimal essential medium (DMEM, Gibco), high glucose, with 10% fetal calf serum and 1% Penicillin-Streptomycin.

To assess chondrocyte function, the expression of collagen-IIα1, aggrecan, metalloproteinase-3 and -13 (MMP3 and MMP13), were analyzed by western blotting. SW1353 cells were treated or not with 10 ng/ml Interleukin-1b for 24 h or 48 h. Protein extracts were prepared in an appropriate buffer containing 150 mM NaCl, 1.0% IGEPAL CA-630, 0.5% sodium deoxycholate, 0.1% SDS, 50 mM Tris, pH 8.0, Complete EDTA-free protease inhibitor mixture (Roche), 1 mM PMSF, 1 mM NaVO3, 5 mM NaF and 3 mM β-glycerophosphate and phosphatase inhibitors (Roche). 40 μg of total proteins were loaded, according to BCA quantification. Proteins were separated by SDS-PAGE electrophoresis, in commercial 4-12% acrylamide gels (Thermo Fisher Scientific) and transferred onto PVDF membranes (Thermo Fisher Scientific) by wet electrophoretic transfer. Blots were blocked 1 hour at RT with 5% bovine serum albumin (Sigma-Aldrich) in TBS-tween (0.5M Tris, 1.5M NaCl, 0.01% Tween) solution and incubated overnight at 4° C. with primary antibodies. Secondary antibodies were incubated 1 hr at RT. The following antibodies were used: anti-collagen-II al (1:1000, Abcam), anti-aggrecan (1:1000, Abcam), anti-MMP-3 (1:1000, Abcam), anti-MMP-13 (1:1000, Abcam). Secondary HRP-conjugated antibodies were purchased from Cell Signalling and used at 1:5000 dilution. Then the content collagen-IIα1, aggrecan, MMP3 and MMP13 were quantified with densitometry and normalized on the content of GAPDH (detected with anti-GAPDH, 1:5000, Cell Signaling)

To ablate the protein expression of the mitochondrial calcium uniporter (MCU), SW1353 cells were transfected with an engineered vector for MCU knockdown, produced by Sirion Biotech. Three days after infection, the expression of MCU was quantified by western blot and densitometric analysis, as previously described. The content of MCU was normalized on the content of the mitochondrial protein TOM20. The following antibodies were used: anti-MCU (1:1000, Sigma-Aldrich), anti-TOM20 (1:5000, Cell Signaling).

To quantify the effect of Interleukin-1β on cell death in SW1353 cells, kinetic experiments of apoptosis were performed with the IncuCyte ZOOM instrument (Essen Bioscience, Ann Arbor, MI, USA). Cells were seeded at 50% confluence in 96-well-plate format in DMEM medium. After 24 h, cells were incubated with IncuCyte Annexin-V Green (4642), according to supplier's instructions and treated with IL-1β. Four images per well were collected at the indicated time using a 10× objective and bandwidth filters (Ex: 440/80 nm; Em: 504/44 nm). Data were exported as area (μm2) per well covered by Annexin-V positive objects and normalized for the total area covered by the cells.

To measure mitochondrial membrane potential, SW1353 cells were seeded in 96-well plates at a density of 8000 cells per well in Growth medium (DMEM high glucose, Gibco) with 10% fetal calf serum. After 24 h, cells were treated with 10 ng/ml of IL-1β for the number of days indicated in the FIG. 7. Then, cells were loaded with the fluorescent mitochondrial membrane potential sensor JC-10. Fluorescence was acquired with MetaXpress Confocal (Molecular Devices) at following emission wavelengths: 590 nm (excitation at 540 nm) and 525 nm (excitation 490 nm), according to supplier's instructions. The ratio fluorescence at 590 nm/525 nm is proportional to change in the mitochondrial membrane potential.

To measure mitochondrial calcium in SW1353 cells were carried out with the same procedure used for HeLa cells. The synergistic effect of quercetin and oleuropein in the osteoarthritic chondrocyte cell model was quantified as described for Hela cells.

Results

Figure 2:
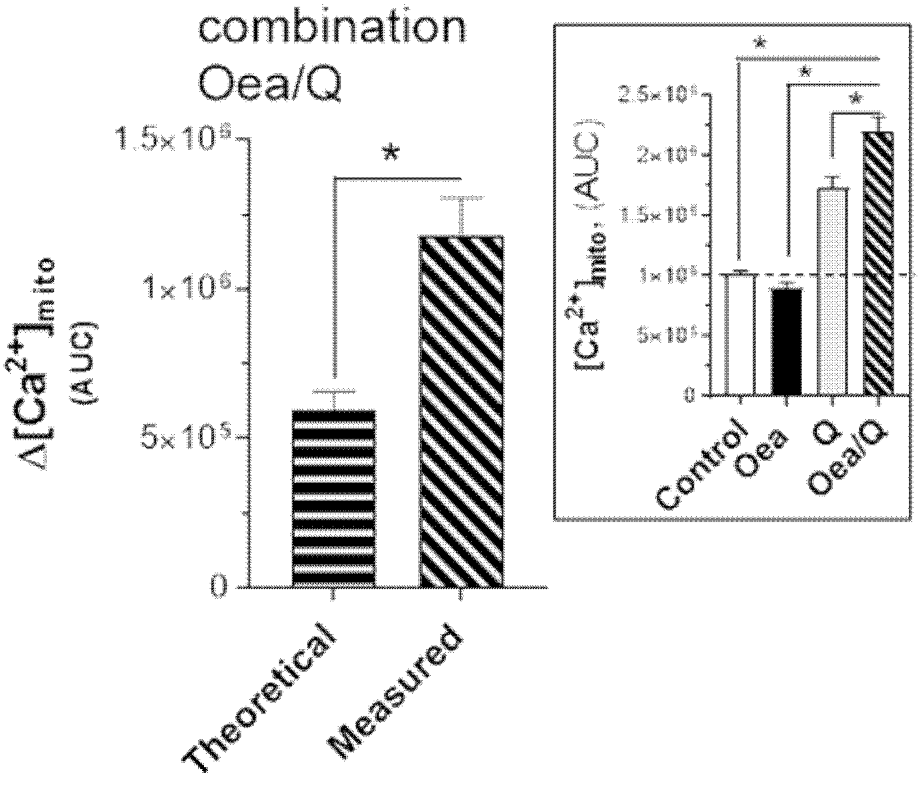
FIG. 2 is a graph showing that oleuropein aglycone (Oea) synergies with Quercetin (Q) to activate mitochondria via mitochondrial Ca2+ rise, in stimulated HeLa cells. The inset shows the effect of oleuropein aglycone (3 μM, black), quercetin (3 μM, gray) and the combination of 3 μM Oea+3 μM Q (Oea/Q), on the integrated mitochondrial calcium rise, evoked by 100 μM histamine. The data in the inset were used to determine, in the main figure, the expected theoretical effect (sum between Oea effect and quercetin effect) and the real measured effect of the combination (Oea+quercetin, Oea/Q) and to extrapolate the synergism. Results are expressed as mean+/−SEM from n=6-9 experiments. * indicates statistically significant difference of the measured vs. theoretical difference in mitochondrial calcium at P<0.05 (Student's t-test).
Figure 3:
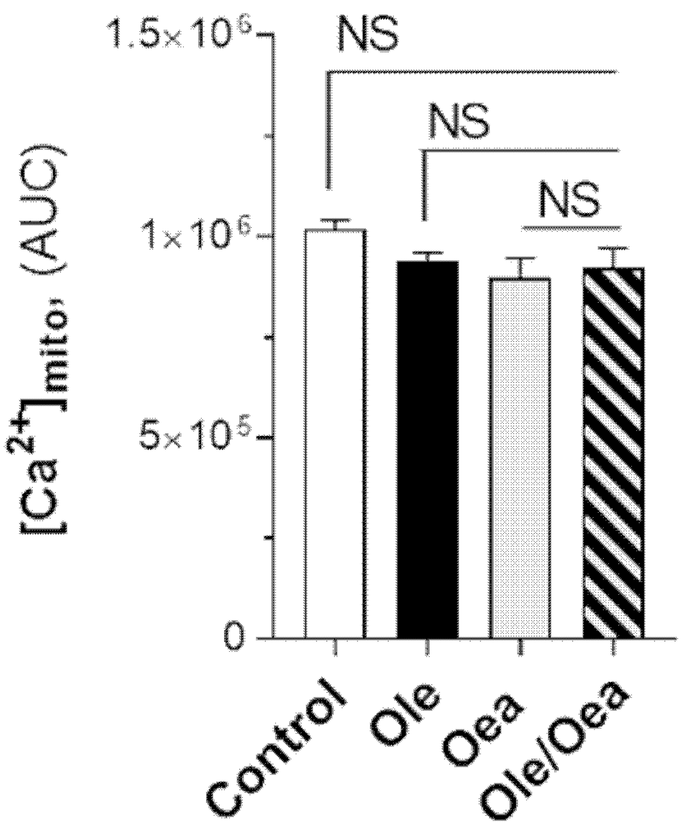
FIG. 3 is a graph showing that Oleuropein (Ole) does not synergies with Oleuropein aglycone (Oea) to activate mitochondria via mitochondrial Ca2+ rise, in stimulated HeLa cells. The bar chart shows the effect of oleuropein (3 μM, black), oleuropein aglycone (3 μM, gray), and the combination of 3 μM Ole+3 μM Oea (Ole/Oea) on the integrated mitochondrial calcium rise, evoked by 100 μM histamine. Results are expressed as mean+/−SEM from n=6-9 experiments. * indicates statistically significant difference of the measured vs. theoretical difference in mitochondrial calcium at P<0.05 (one-way ANOVA test).
Figure 4:
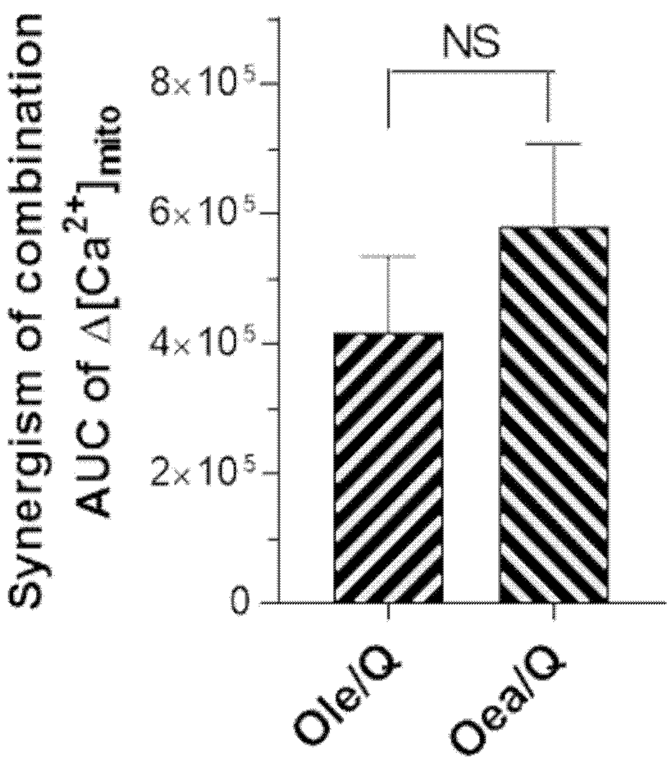
FIG. 4 is a graph showing that Oleuropein (Ole) and Oleuropein aglycone (Oea) promote the same level of synergism in combination with Quercetin (Q). The synergisms were calculated as described in FIG. 1 and FIG. 2. Results are expressed as mean+/−SEM from n=6 experiments. NS, not significant, indicates no statistically significant difference between the two group (combinations) at P<0.05 (Student's t-test).

As shown in FIG. 1 oleuropein synergizes with quercetin to activate mitochondria, by increasing mitochondrial calcium elevation in Hela cells, during stimulation. As shown in FIG. 2, also oleuropein aglycone synergizes with quercetin to activate mitochondria, by increasing mitochondrial calcium elevation in Hela cells, during stimulation. Instead, as shown in FIG. 3, oleuropein does not synergize with oleuropein aglycone to activate mitochondria, via mitochondrial calcium elevation in Hela cells. As shown in FIG. 4, oleuropein and oleuropein aglycone promote the same level of synergism in combination with quercetin.

Figure 5:
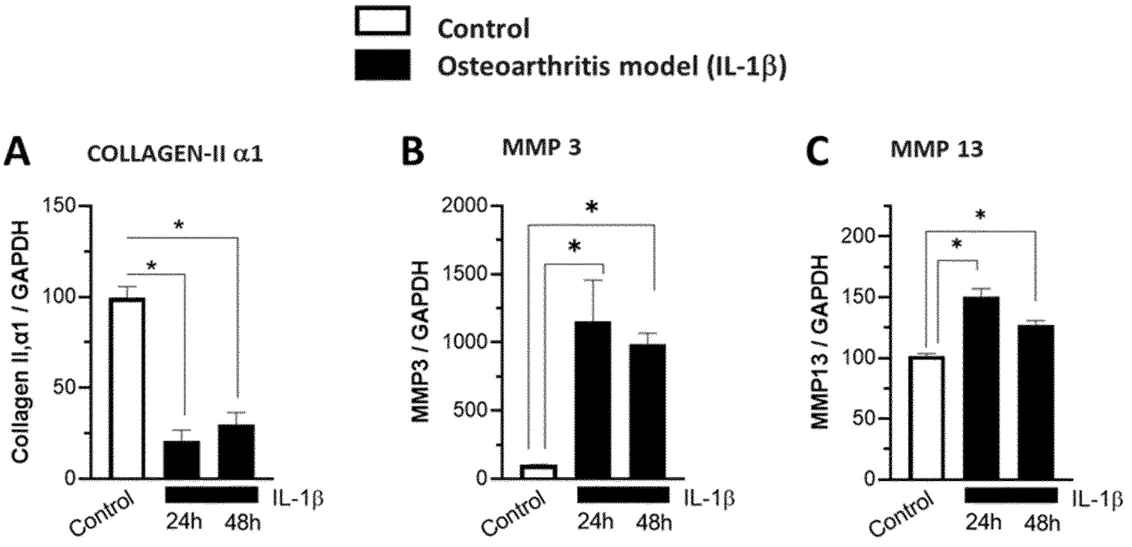
FIG. 5 shows that an "in vitro" model of osteoarthritic chondrocytes (SW1353 cells, treated with the pro-inflammatory cytokine Interleukin-1β, IL-1β) reveals dysfunctional chondrocytes. Therefore.
Figure 6:
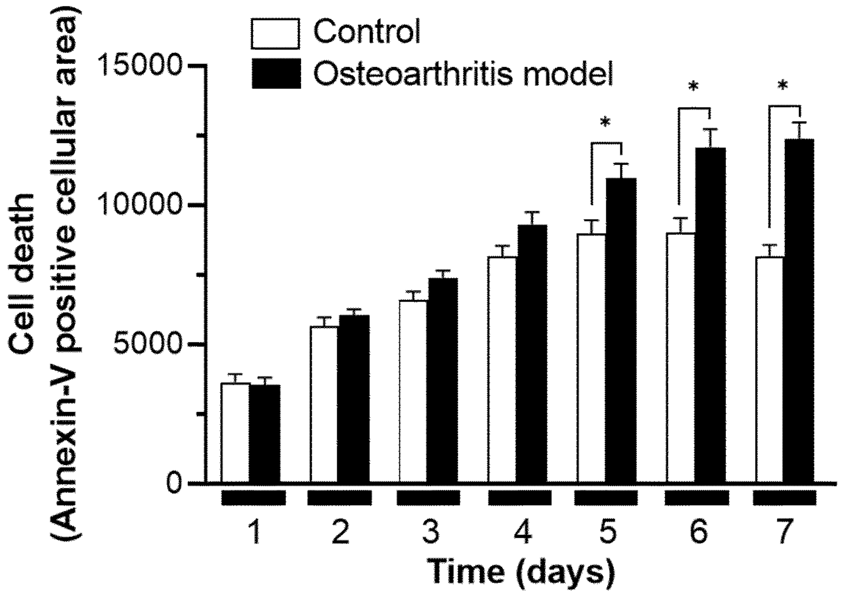
FIG. 6 shows that an "in vitro" model of osteoarthritic chondrocytes (SW1353 cells treated with IL-1β) reveals increased cell death of SW1353 chondrocytes. Therefore, the Annexin-V positive cells significantly increased after 5 days of IL-1β treatment, as indicated. Results are expressed as mean+/−SEM from n=11 experiments per condition. * indicates statistically significant difference of control vs. SW1353 cells treated with IL-1β, at the indicated time points, at P<0.05 (Student's t-test).
Figure 7:
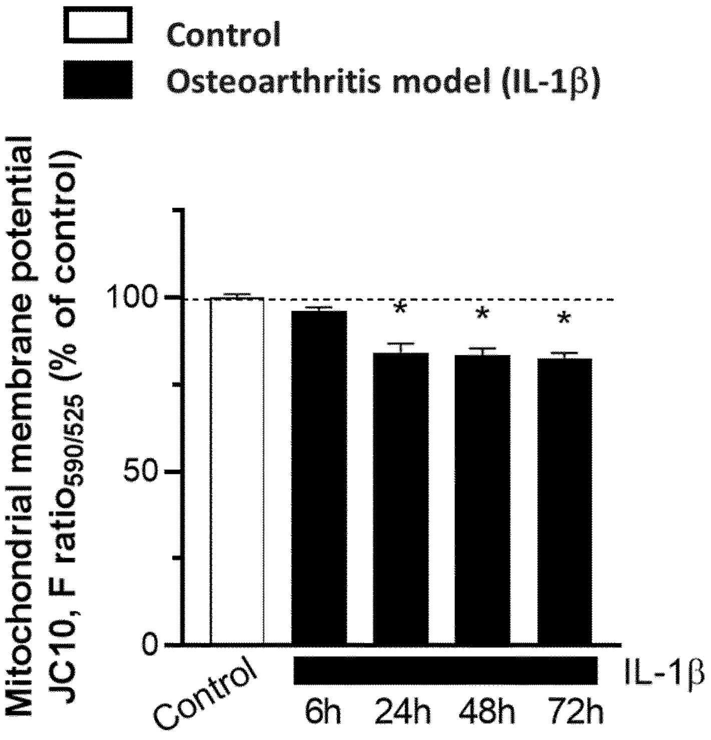
FIG. 7 shows that an "in vitro" model of osteoarthritic chondrocytes (SW1353 cells treated with IL-1β) reveals dysfunctional mitochondria with impaired mitochondrial membrane potential. Therefore the ratio fluorescence (at 590/525 nm) of the mitochondrial membrane potential sensor JC10 significantly decreases after 24 h of IL-1β, indicating decrease energization of mitochondria. Results are expressed as mean+/−SEM from n=8 experiments per condition. * indicates statistically significant difference of control vs. SW1353 cells treated with IL-1β, at the indicated time points, at P<0.05 (One-way ANOVA test).
Figure 8:
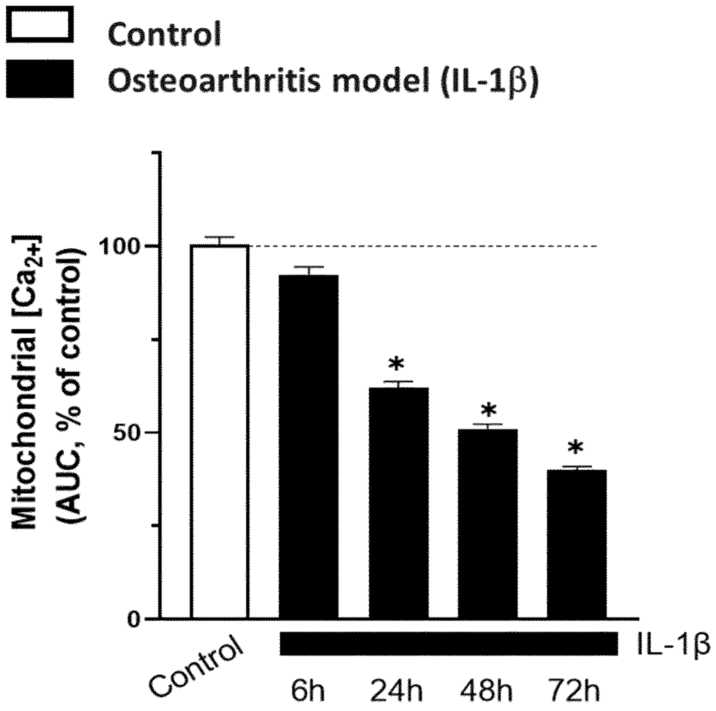
FIG. 8 shows that an "in vitro" model of osteoarthritic chondrocytes (SW1353 cells treated with IL-1β) reveals dysfunctional mitochondria with impaired mitochondrial calcium uptake, during stimulation. The graph shows that the mitochondrial $Ca^{2+}$ rise stimulated by agonist (histamine), decrease in SW1353 cells treated with IL-1β at the indicated time points. Results are expressed as mean+/−SEM from n=46-96 experiments per condition. * indicates statistically significant difference of control vs. SW1353 cells treated with IL-1β, at the indicated time points, at P<0.05 (One-way ANOVA test).
Figure 9:
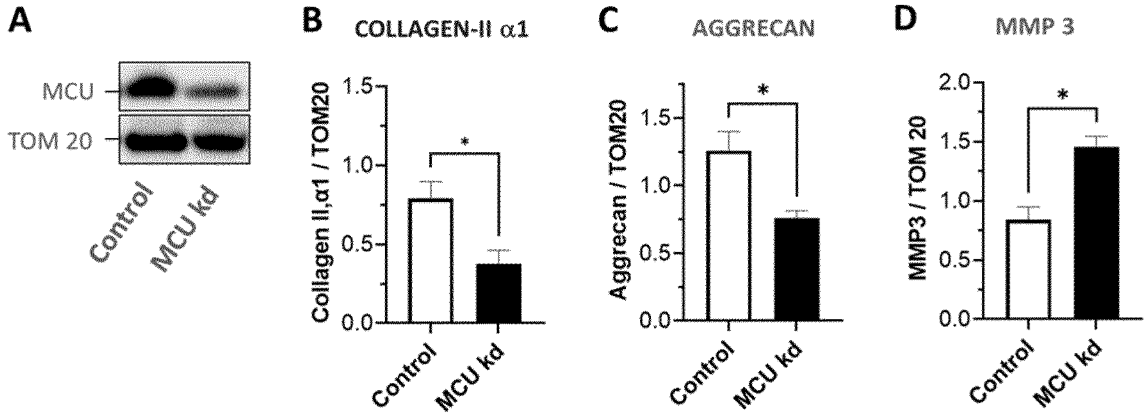
FIG. 9 shows that an "in vitro" genetic model of chondrocytes (SW1353 cells) with dysfunctional mitochondrial calcium uptake (MCU-Knockdown, MCU-kd) reveals impaired chondrocyte function.

As shown in FIG. 5 a cellular model of osteoarthritic chondrocytes reveals dysfunctional chondrocytes, given that collagen-IIα1 content is strongly decreased, compared with control (non-osteoarthritic chondrocytes, FIG. 5A), and the expression of metalloproteinases MMP3 (FIG. 5B) and MMP13 (FIG. 5C) is increased. Consistently, these dysfunctional osteoarthritic chondrocytes are characterized by increased cell death (FIG. 6). As shown in FIG. 7, the mitochondria function is impaired in this cellular model of osteoarthritic chondrocytes, given that the mitochondrial membrane potential decreases. Reliably, the mitochondrial calcium elevation is strongly decreased during stimulation in this cellular model of osteoarthritic chondrocytes (FIG. 8). As shown in FIG. 9, a genetic model of chondrocytes with dysfunctional mitochondrial calcium uptake (MCU-Knockdown, kd, FIG. 9A) reveals impaired chondrocyte function, mimicking the effect of osteoarthritis. Therefore collagen-IIα1 expression (FIG. 9B) and aggrecan expression are decreased (FIG. 9C) in MCU-kd cells, whereas the expression of metalloprotease MMP3 is increased.

Figure 10:
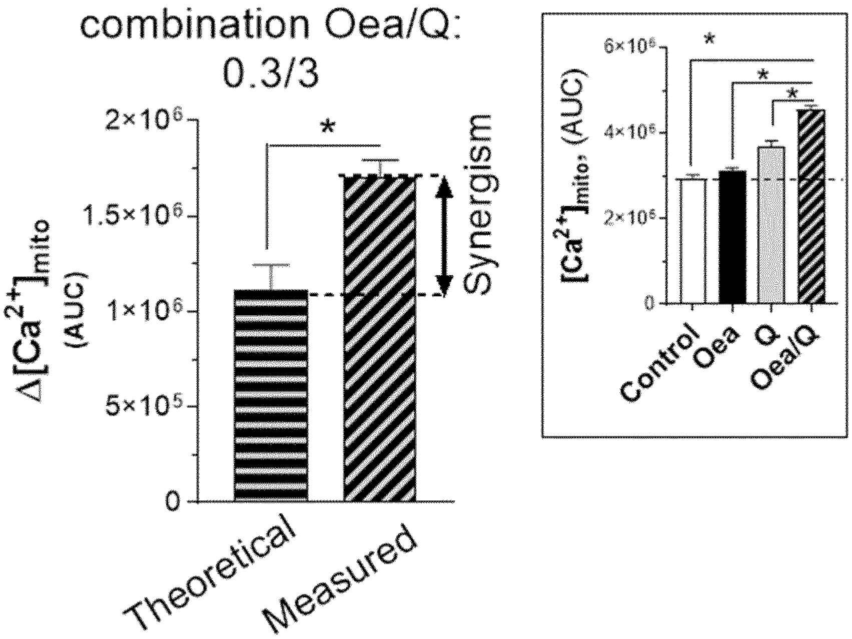
FIG. 10 is a graph showing that oleuropein aglycone (Oea) synergies with Quercetin (Q) to activate mitochondria via mitochondrial Ca2+ rise, in a cellular model of osteoarthritic chondrocytes, described in the previous figures (SW1353 cells treated with IL-1β). The inset shows the effect of oleuropein aglycone (0.3 μM, black), quercetin (3 μM, gray) and the combination of 0.3 μM Oea+3 μM Q (Oea/Q), on the integrated mitochondrial calcium rise, evoked by 100 μM histamine. The data in the inset were used to determine, in the main figure, the expected theoretical effect (sum between Oea effect and quercetin effect) and the real measured effect of the combination (Oea+quercetin, Oea/Q). * indicates statistically significant difference of the measured vs. theoretical difference in mitochondrial calcium at P<0.05 (Student's t-test).
Figure 11:
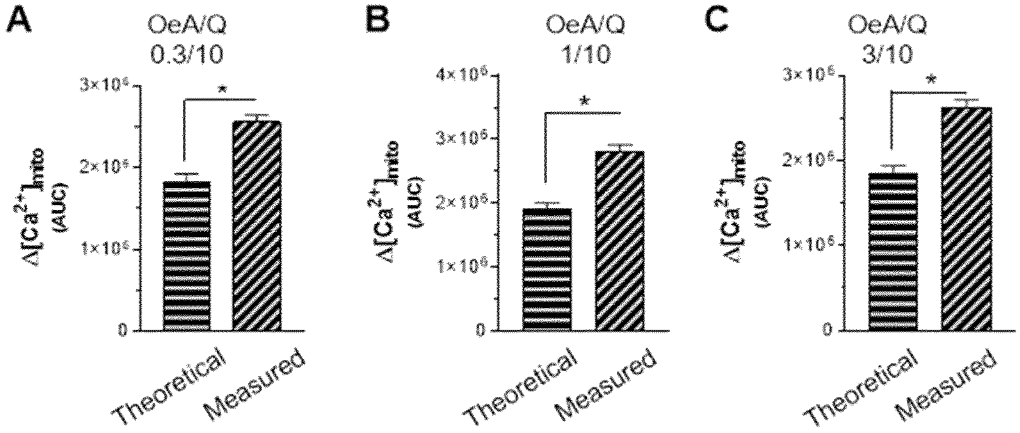
FIG. 11 is a graph showing that several combinations of oleuropein aglycone (Oea with Quercetin (Q) synergize to activate mitochondria, via mitochondrial Ca2+ rise, in the cellular model of osteoarthritic chondrocytes, described in the previous figures (SW1353 cells treated with IL-1β). The amount of Oea and Q is indicated in the upper part of each panel (A,B,C) and it is expressed in micromolar (μM). The expected theoretical effect (sum between Oea effect and quercetin effect) and the real measured effect of the combination (Oea+quercetin, Oea/Q), were measured as described in FIG. 10 and they are here compared to extrapolate the synergism. Results are expressed as mean+/−SEM from n=7 experiments for each condition. * indicates statistically significant difference of the measured vs. theoretical difference in mitochondrial calcium at P<0.05 (Student's t-test).

Finally, as shown in FIG. 10, Oleuropein aglycone (Oea) synergies with Quercetin (Q) to activate mitochondria via mitochondrial Ca2+ rise, in the described cellular model of osteoarthritic chondrocytes (SW1353 cells treated with IL-1b). As shown in FIG. 11, several combinations of Oleuropein aglycone (Oea) with Quercetin (Q) synergize to activate mitochondria, via mitochondrial Ca2+ rise, in the described cellular model of osteoarthritic chondrocytes.

The invention claimed is:

1. A method for preventing or treating cartilage degeneration by increasing mitochondrial calcium elevation in an individual in need thereof, the method comprising administering to the individual a composition comprising an effective amount of a combination of oleuropein aglycone, elenolic acid, homovanillyl alcohol, isohomovanillyl alcohol, and quercetin and/or a derivative thereof, and the composition is administered in a dose comprising an amount of the oleuropein aglycone and the quercetin and/or derivative thereof that synergistically activate mitochondria by mitochondrial calcium rise.

2. The method according to claim 1, wherein the derivative of quercetin is selected from the group consisting of quercetin 3-O-galactoside, quercetin 3-O-glucoside (izoquercetin), quercetin 3-O-xyloside, quercetin 3-O-rhamnoside (quercitrin), quercetin 3-O-glucuronide, quercetin 7-O-glucoside, quercetin 3-O-diglucoside, quercetin 3,4'-diglucoside, quercetin 3-O-rhamnoside-7O-glucoside, quercetin 3-O-rutinoside (rutin), quercetin3-O-6"-acetylglucoside, quercetin 3-methyl ether, quercetin 3,3'-dimethyl ether, and mixtures thereof.

3. The method according to claim 1, wherein the composition further comprises calcium.

4. The method according to claim 1, wherein the composition further comprises at least one compound selected from the group consisting of antioxidants, anti-inflammatory compounds, glycosaminoglycans, prebiotics, fibres, probiotics, fatty acids, enzymes, minerals, trace elements and vitamins.

5. The method according to claim 1, wherein the composition is selected from the group consisting of food compositions, dietary supplements, nutritional compositions, oral nutritional supplement, medical food, nutraceuticals, beverages, powdered nutritional products to be reconstituted in water or milk before consumption, food additives, food for special medical purpose (FSMP) medicaments, drinks, petfood, and combinations thereof.

6. The method according to claim 1, wherein the composition is in a form selected from the group consisting of a solid powder, a powdered stick, a capsule and a solution.

7. The method according to claim 1, wherein the administering of the composition has at least one effect selected from the group consisting of i) maintaining or improving joint functionality, including cartilage functionality, during ageing; and ii) decrease joint pain, including inflammatory and/or nociceptive pain.

8. The method according to claim 1, wherein the administering of the composition improves activity and/or mobility of the individual.

9. The method according to claim 1, wherein the administering of the composition inhibits or decreases cartilage degeneration in Osteoarthritis.

10. The method according to claim 1, wherein the individual is an older adult or an elderly individual.

11. The method according to claim 1, wherein the quercetin is isolated and/or chemically synthesized.

12. The method according to claim 3, wherein at least a portion of the calcium is present in one or more calcium salts selected from the group consisting of calcium acetate, calcium carbonate, calcium chloride, calcium citrate, calcium glubionate, calcium gluconate, and calcium lactate.

13. The method according to claim 3, wherein 0.1 g to 1.0 g of the calcium is administered to the individual per day.

* * * * *